(12) United States Patent
Bidarahalli et al.

(10) Patent No.: US 6,990,574 B2
(45) Date of Patent: Jan. 24, 2006

(54) OBJECT ORIENTED FRAMEWORK FOR SCANNER/WORKSTATION CONFIGURATION

(75) Inventors: Phani Kumar Bidarahalli, Waukesha, WI (US); Christopher J. Mussack, Waukesha, WI (US); Rebecca J. Schleicher, Greenfield, WI (US)

(73) Assignee: General Electric Company, Schenectady, NY (US)

( * ) Notice: Subject to any disclaimer, the term of this patent is extended or adjusted under 35 U.S.C. 154(b) by 464 days.

(21) Appl. No.: 09/846,816

(22) Filed: May 1, 2001

(65) Prior Publication Data

US 2002/0166046 A1 Nov. 7, 2002

(51) Int. Cl.
G06F 9/445 (2006.01)
(52) U.S. Cl. .......................................... 713/2
(58) Field of Classification Search ............... 713/2
See application file for complete search history.

(56) References Cited

U.S. PATENT DOCUMENTS 5,689,708 A * 11/1997 Regnier et al. ............. 709/229
6,119,186 A * 9/2000 Watts et al. ................. 710/104
6,202,121 B1 * 3/2001 Walsh et al. ................ 711/100
6,476,833 B1 * 11/2002 Moshfeghi .................. 345/854
6,502,123 B1 * 12/2002 Gulick ....................... 718/102
6,530,081 B1 * 3/2003 Hayes, Jr. ................... 717/176

OTHER PUBLICATIONS

"Windows95 Resource Kit". 1995. Microsoft Press. pp. 479, 482-483, 504-506, 512.*

* cited by examiner

Primary Examiner—Lynne H. Browne
Assistant Examiner—Eric Chang
(74) Attorney, Agent, or Firm—Quarles & Brady LLP; Carl Horton

(57) ABSTRACT

A method and apparatus for rapidly configuring a medical imaging system with applications that are preferred by specific system users, the method including, at the beginning of an imaging session, receiving user information and using the information to identify user preferred applications, determining which of the preferred applications is already booted, booting un-booted preferred applications and disabling non-preferred booted applications so that only preferred applications are booted during the next imaging session.

18 Claims, 6 Drawing Sheets

Critical Applications Database 152

| Application | Critical App |
|---|---|
| 1 | 5,6 |
| 2 | NA |
| 3 | 2,12 |
| 4... | . |
| . | . |
| . | . |
| . | . |
| NN | XX |

User Preferred Applications Database 158

| User | Preferred Apps |
|---|---|
| 00001 | 1,2,*5,6*,12,17,20 |
| 00002 | 1,2,4,5,6,7,8,9,10,11 |
| 00003 | *2*,3,*12* |
| . | . |
| . | . |
| . | . |
| NNNNN | X,X,X,X |

OBJECT ORIENTED FRAMEWORK FOR SCANNER/WORKSTATION CONFIGURATION

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The field of the invention is medical imaging systems and more specifically start-up protocols for medical imaging system workstations.

Herein, while it is recognized that physicians often work through radiologists to generate images using imaging systems, to simplify this explanation each unique radiologist/physician pair (i.e., a unique combination of a radiologist and a physician) will be referred to generically as a "physician". In addition, while the invention may be used with any complex medical imaging system, the invention will be described in the context of a magnetic resonance imaging (MRI) system.

Medical imaging systems have been used for many years to generate diagnostic quality medical images of various types. Exemplary early imaging systems often were only capable of generating images having very similar characteristics (i.e., all images generated by a specific imaging system tended to have similar or identical image quality characteristics, be of the same view, etc.). This was because early imaging systems were relatively simple having only a small number of settable data acquisition and data processing parameters.

Over time data collecting hardware, processing power and software applications have been developed that facilitate extremely complex imaging systems having many different applications. In complex systems often a workstation is provided that runs all of the applications. An exemplary workstation often includes a graphical user interface (GUI), one or more input devices (e.g., a mouse, a keypad, etc.) and either a local or a remotely linked server that runs the applications and controls the imaging system.

In a nuclear magnetic resonance imaging (MRI) system applications include a plurality of image viewer applications, a plurality of data acquisition applications, a plurality of separate data manipulation applications, various data filtering applications, patient data applications (i.e., enabling input and modification of patient information), database browser applications, etc. While a complex imaging system may include a huge number of applications, in order to simplify this explanation it will be assumed that an exemplary imaging system includes 20 applications.

While each complex imaging system may include a huge number of applications, each physician may only require a small sub-set of available applications to perform a typical imaging process. Thus, in the exemplary 20 application system described herein, it will be assumed that a first physician may only require a first sub-set of 7 applications, a second physician requires a second sub-set of 10 applications where the second subset includes 4 of the applications in the first subset and 6 other applications that are not in the first subset, a third physician requires a third application subset including two applications from the first subset and one application that is in neither the first or second subset and so on.

In addition to the plethora of applications that some systems may include, many applications have adjustable parameters that either affect operation of the workstation or final image characteristics. For instance the industry has developed many different filtering kernels for filtering acquired data in different ways to reduce image aliasing to different degrees. Filtering is often computationally intensive and therefore more complex filtering techniques can take an appreciable amount of time to complete.

The degree of acceptable alliasing in an image depends at least in part on what a physician wants to accomplish during an imaging session. Thus, in some cases where general shape of an anatomical object is to be observed a relatively large degree of alliasing may be acceptable whereas in other cases where intricate details of an object have to be observed only a small degree of alliasing may be acceptable.

In almost all imaging sessions processing speed is extremely important to increase system throughput (i.e., the number of imaging sessions that occur in a day), to increase patient comfort and to reduce physician time necessary for imaging and analysis. Thus, whenever possible, imaging protocols that expedite data acquisition and expedite processing and viewing while still rendering images that are suitable for their intended use should be selected. This means that different physicians attempting to accomplish different goals via the imaging system will routinely select different filtering techniques to maximize throughput and while minimizing alliasing.

As another example of physicians selecting different applications, different physicians wanting to examine the same anatomical portion of a patient will often require different image sequences. For instance, a first physician may routinely want to view seven different images sequenced in a specific order for "click-through" viewing via a GUI while a second physician may only want three images sequenced in a different fashion to diagnose the same ailment.

As yet another example, in an MRI system there are many different data acquisition pulse sequences that can be generated that cause different anatomical tissues to be highlighted. Again, different physicians often find different highlighting techniques to be advantageous and therefore the different physicians often require selection of varying pulse sequences.

One other example includes setting preferences related to other physicians that are granted access to images generated by a particular physician. For example, where ten physicians each use a system, one of the ten may want to by default, grant access to images generated by the physician to three of the other physicians. These preferences are currently set each time a physician accesses the system.

Hereinafter preferred applications and preferred preferences are collectively referred to as preferred applications unless indicated otherwise.

In many radiology departments, throughout the course of a day many physicians will use an imaging system. To use an imaging system a physician typically schedules an imaging session and, at the scheduled time, accesses the system workstation and sets up application programming parameters for a specific imaging session. Depending on physician control, all or any subset of the applications may be employed during the imaging session. To this end, despite their operation behind the scenes, often the separate applications are transparent to the physician. Thus, the physician may perform a function that causes three or four or more applications to operate in parallel or in a sequence behind the scenes. At the end of the session the physician may clear all application parameter settings.

During the next imaging session another physician steps through the process described above in a similar fashion, the applications and their orders perhaps differing between the first and second sessions based on physician preferences.

During any imaging session the physician controlling the session is unknown to the system and therefore the system cannot independently determine which of the 20 applications and which application parameters the physician prefers and requires. For instance, during the first imaging session the system cannot determine if the physician is the first, second or third physician described above. Instead, the system simply waits for the physician to specify his preferences.

In order to have all applications ready for use by whichever physician uses the system, upon startup (i.e., when the system is first booted up in the morning), exemplary imaging systems typically boot all system applications. For instance, in the present example, upon startup all 20 applications are booted. In this manner, when a physician accesses the system at the beginning of any subsequent imaging session, no matter which subset of the 20 applications the physician intends to employ, the applications have already been booted up and are ready for use. Thus, the physician can simply begin setting application parameters and then run the preferred applications.

While systems like the one described above facilitate rapid application employment after the initial startup process, such systems have several shortcomings. First, because all applications are booted upon initial startup, the startup process duration is relatively long and therefore can delay the first imaging session.

Second, booting up all applications and maintaining all of the applications in a supported state has adverse affects on system performance. To this end, while a subset of applications may all be performable to support an imaging function, sometimes a reduced set of functions may be able to perform essentially the same function but with slightly different results. For instance, while each of 10 applications may be applicable to a specific function, some physicians may require only 5 of the applications to obtain an image for the intended purpose. In this case, while an automated system may use all 10 applications, performance could be enhanced by using only the preferred 5 applications.

Increasing the number of simultaneously running applications increases the time required to complete an application cycle for any one of the applications being performed. Thus, where 10 applications are booted and are performed during an imaging session the session duration will typically be longer than the session duration where only 5 applications are performed.

Even where applications are not in current use and therefore do not affect data processing speed, the fact that the applications are booted up means that they reside on a system memory. Such application storage itself reduces system performance as additional data swapping is required to manage collected data during processing.

Moreover, in cases where several applications run in parallel, it may be that only a subset of the running applications is critical while others of the running applications are not critical. For instance, during data acquisition, it is advantageous if the data acquisition applications remain fully supported so that all potential data is collected while other applications such as processing of the raw data can be performed, if necessary, at a later time. If acquisition applications are not fully supported the result may be to prolong the data acquisition process. As indicated above, in all imaging processes patient comfort is increased and potential movement is minimized by reducing acquisition process duration and therefore process duration should be minimized whenever possible.

Third, even though user preferred applications are booted prior to a physician accessing the system and thus are ready to go upon access, preferred preferences still have to be separately set for each physician. This process is time consuming and reduces system throughput.

To ensure support for critical applications when a processor becomes bogged down, some systems are programmed to suspend or shut down non-critical applications so that the critical applications can remain fully supported. For instance, during data acquisition, when a processor reaches a threshold central processor unit (CPU) saturation (e.g., 75%), the processor turns off non-critical applications so that critical applications remain fully supported. While this "load thresholding" feature is advantageous, this feature is typically programmed into the system and, as with the applications that are booted, cannot be modified (i.e., criticality cannot be modified, % threshold cannot be modified, etc.) to support separate preferences of each physician.

BRIEF SUMMARY OF THE INVENTION

An exemplary embodiment of the invention includes a method for configuring a set of applications in a medical imaging system, the method comprising the steps of receiving system user identifying information, using the identifying information to determine the user's preferred applications, determining which of the preferred applications are already booted up, the already booted up preferred applications being a first subset and the other preferred applications being a second subset and booting up the second subset of preferred applications.

In one embodiment the method further includes the steps of, after the step of using, identifying non-preferred applications that are booted and disabling the non-preferred applications. The step of disabling may include either turning off the non-preferred applications or minimizing the applications so that, while booted, the applications are not performed. Any other disabling process that renders an application dormant is also contemplated.

The method may be used with a database including user-identifying information correlated with preferred applications wherein the step of using includes correlating the identifying information with the preferred applications. The step of receiving may include providing at least one field for entering user identifying information on a display and, when information is provided via the field, retrieving the information therefrom.

In one aspect at least one critical application is critical to operation of at least one of the preferred applications and the method further includes the steps of, for each preferred application, determining if there are any critical applications and for critical applications determining which of the critical applications is booted up, the booted up critical applications being a first subset of critical applications and all other critical applications being a second subset of critical applications, the method further including booting up all second subset critical applications.

The method may also be for configuring the user preferred applications, the method further including the steps of, providing an interface for receiving user information and preferences, receiving user preferences and related user information via the interface and storing the user preferred applications correlated with the user information for subsequent use. In another aspect there may be at least one critical application that is critical to operation of at least one user specified preferred application and the method may further include the steps of, for each specified preferred application, determining if there are any critical applications and, where there is at least one critical application, adding the critical application to the preferred applications for the user.

The system includes a processor for running the applications and the method may also be for modifying the booted applications as a function of processor usage and, wherein, the method further includes the steps of, after the applications are booted and during system use, monitoring processor usage and, when processor usage exceeds a threshold level, disabling at least one of the booted applications.

The invention also includes a processor for use in configuring a set of applications in a medical imaging system, the processor running a pulse sequencing program to perform steps comprising receiving system user identifying information, using the identifying information to determine the user's preferred applications, determining which of the preferred applications are already booted up, the already booted up preferred applications being a first subset and the other preferred applications being a second subset and booting up the second subset of preferred preferences.

In one embodiment the pulse-sequencing program causes the processor to further perform the steps of, after the step of using, identifying non-preferred applications that are booted and disabling the non-preferred applications.

The processor may also be for use with a database including user-identifying information correlated with preferred applications. Here the step of using may include correlating the identifying information with the preferred applications.

In some cases there may be at least one critical application is critical to operation of at least one of the preferred applications. In this case the program may further cause the processor to perform the steps of, for each preferred application, determining if there are any critical applications and for critical applications determining which of the critical applications is booted up, the booted up critical applications being a first subset of critical applications and all other critical applications being a second subset of critical applications, the processor further including booting up all second subset critical applications.

The processor may also be for specifying the user preferred applications, the program further causing the processor to perform the steps of, providing an interface for receiving user information and preferences, receiving user preferences and related user information via the interface and storing the user preferred applications correlated with the user information for subsequent use.

The invention further includes a method for configuring a set of applications in a medical imaging system, the method comprising the steps of receiving system user identifying information, using the identifying information to determine the user's preferred applications, determining which of the preferred applications are already booted up, the already booted up preferred applications being a first subset and the other preferred applications being a second subset, booting up the second subset of preferred preferences, identifying non-preferred applications that are booted and disabling the non-preferred applications.

Furthermore the invention includes a method for specifying a set of user preferred applications in a medical imaging system wherein at least one critical application is critical to operation of at least one other application, the method comprising the steps of receiving system user identifying information, receiving user preference information indicating at least one user preferred application, storing the user identifying information correlated with the user preferred applications for subsequent system configuration upon booting, determining if there are any applications that are critical to the user preferred applications and where an application is critical to a user preferred application, adding the critical application to the user stored preferred applications correlated with the user.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE SEVERAL VIEWS OF THE DRAWINGS

FIG. 5 is a schematic diagram of a table stored in one of the databases of FIG. 1;

FIG. 6 is a schematic diagram of a another table stored in one of the databases of FIG. 1.

DETAILED DESCRIPTION OF THE INVENTION

Figure 1:
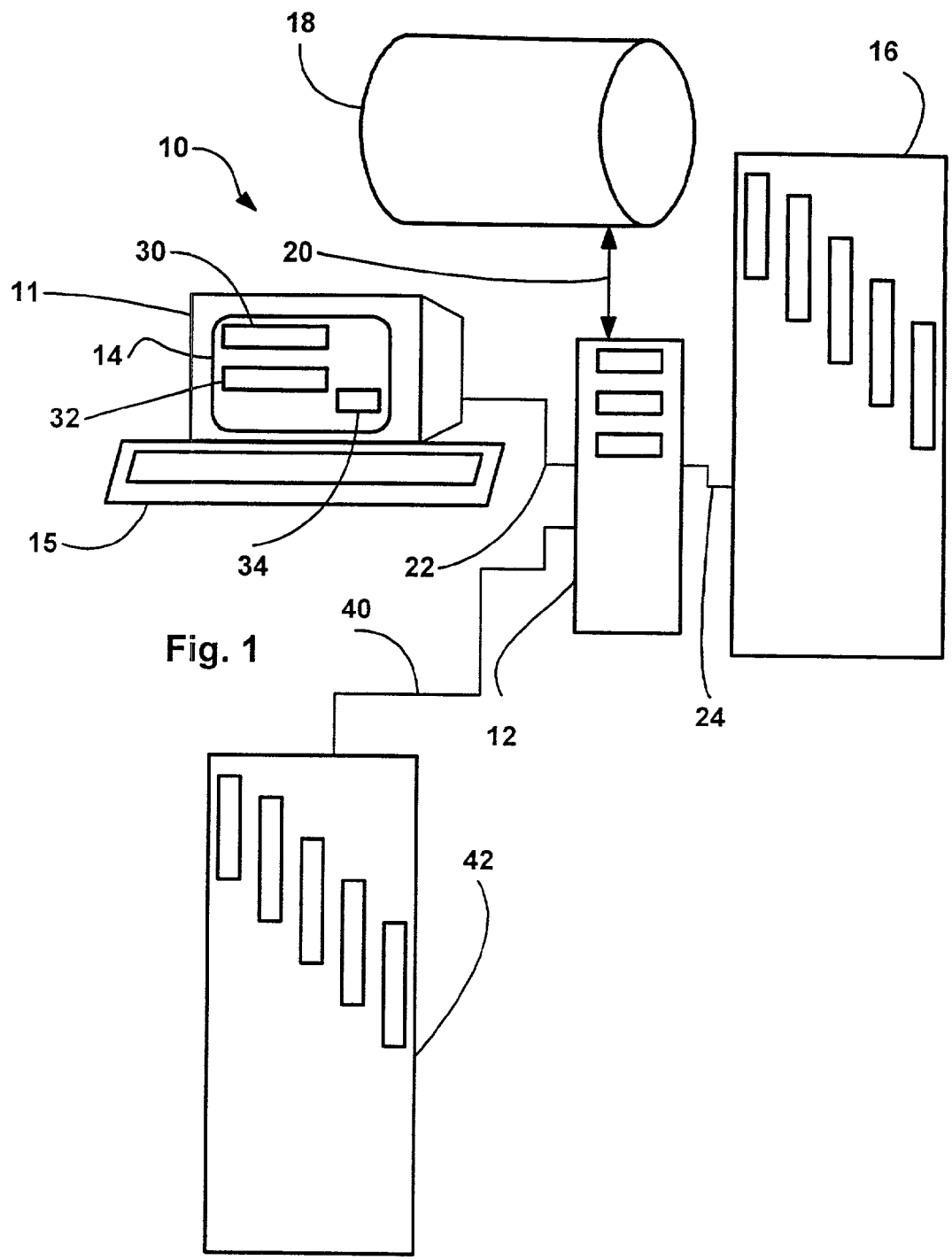
FIG. 1 is a schematic view of an imaging system according to the present invention.

Referring now to the Figures the present invention will be described in the context of the exemplary and simplified imaging system 10 illustrated in FIG. 1. It should be understood that while the system in FIG. 1 has been illustrated in a simplified format and will be described generally as an MRI system in order to simplify this explanation, the invention is meant to be useable with any imaging system wherein many applications may be used on the system, where a single system is to be used by many different users, where processing speed is particularly important and where the system is not shut down between consecutive system uses.

System 10 in FIG. 1 includes a workstation 11, a server 12, a local database 16, a remote database 40 and MRI imaging hardware 18 (referred to hereinafter as system 18). Workstation 11 includes an interface 14 and an input device 15, preferably in the form of a keyboard. Other input devices may be used in addition to or in lieu of a keyboard including a mouse or some similar device. Interface 14 is a display screen that is used for several different purposes including specifying a user's application preferences (i.e., preferred applications), interacting with various applications during data acquisition and data manipulation, controlling various settings and operation of system 18 and also for viewing system generated images. Workstation 11 is linked to server 12 via a bus 22.

While server 12 is shown as a simple server to simplify this explanation, server 12 often comprises several servers or processing systems that together perform various imaging functions. To this end, because system 18 is an MRI system, server 12 typically will include a system 18 controller for controlling gradient coil and other signals, a physiological acquisition controller, a patient positioning system controller, an image processor and other control systems. For a better understanding of the functions performed by server 12 refer to U.S. Pat. No. 6,064,205 that is commonly owned with the present invention and is incorporated herein by reference. Server 12 is capable of running any of several different applications or subsets of applications during acquisition and/or data manipulation. Server 12 is linked via a two way bus to system 18 for controlling system 18 during acquisition and for receiving acquired data for storage and either simultaneous or subsequent manipulation.

System 18 includes various coils and other systems as well known in the MRI art and as described in more detail in the above referenced and incorporated U.S. patent.

Server 12 is also linked to each of databases 16 and 42. Link 24 between server 12 and database 16 is a two-way high-speed data bus. Database 16 is a local database and is used to store currently booted applications and data that is either currently being acquired or is currently being manipulated. Link 40 is a computer network link (i.e. a wide area or local area network link or perhaps an Internet link). Database 40 is a remote database that is used to archive image data and also for storing all application software code independent of whether or not the applications are booted on server 12. Database 42 may be accessible to more than server 12 so that other servers and imaging systems can gain access to image data and applications stored on database 42. While shown as similar components, database 42 is typically much larger than database 16 so that database 42 can store massive amounts of data and all application code.

Referring now to FIGS. 1, 5 and 6 two separate tables of sub-databases 150 and 156 that are stored on one of databases 16 or 42 are illustrated. Preferably, so as to reduce the amount of configuration information stored on local database 16, sub-databases 150 and 156 are stored on remote database 42. Database 150 is a critical application database that correlates certain applications with other applications that have to be booted in order to support the correlated applications. To this end database 150 includes an applications column 152 and a critical applications column 154. Applications column 152 lists all possible system applications. For instances, column 152 lists applications 1, 2, 3, 4, . . . NN applications.

For each application in column 152, column 154 lists all critical applications. For instance, for application 1 in column 152 there are two applications, 5 and 6, listed in column 154, as being critical. Similarly, for application 3 in column 152 there are two applications, 2 and 12, that are listed as critical in column 154. For application 2 in column 152 there are no critical applications (i.e., an NA appears in column 154).

Database 156 is a User Preferred Applications Database that correlates specific system 10 (see FIG. 1) users with preferred applications. To this end database 156 includes two columns 158 and 160. Column 158 lists all system 10 users in an abbreviated form including users 00001, 00002, 00003, . . . NNNNN. For each user in column 158, column 160 lists all preferred applications. For example, for user 00001 in column 158, column 160 indicates applications 1, 2, 5, 6, 12, 17 and 20, for user 00002 column 160 indicates applications 1, 2, 4, 5, 6, 7, 8, 9, 10 and 11 and for user 00003 column 160 lists applications 2, 3 and 12.

Figure 2:
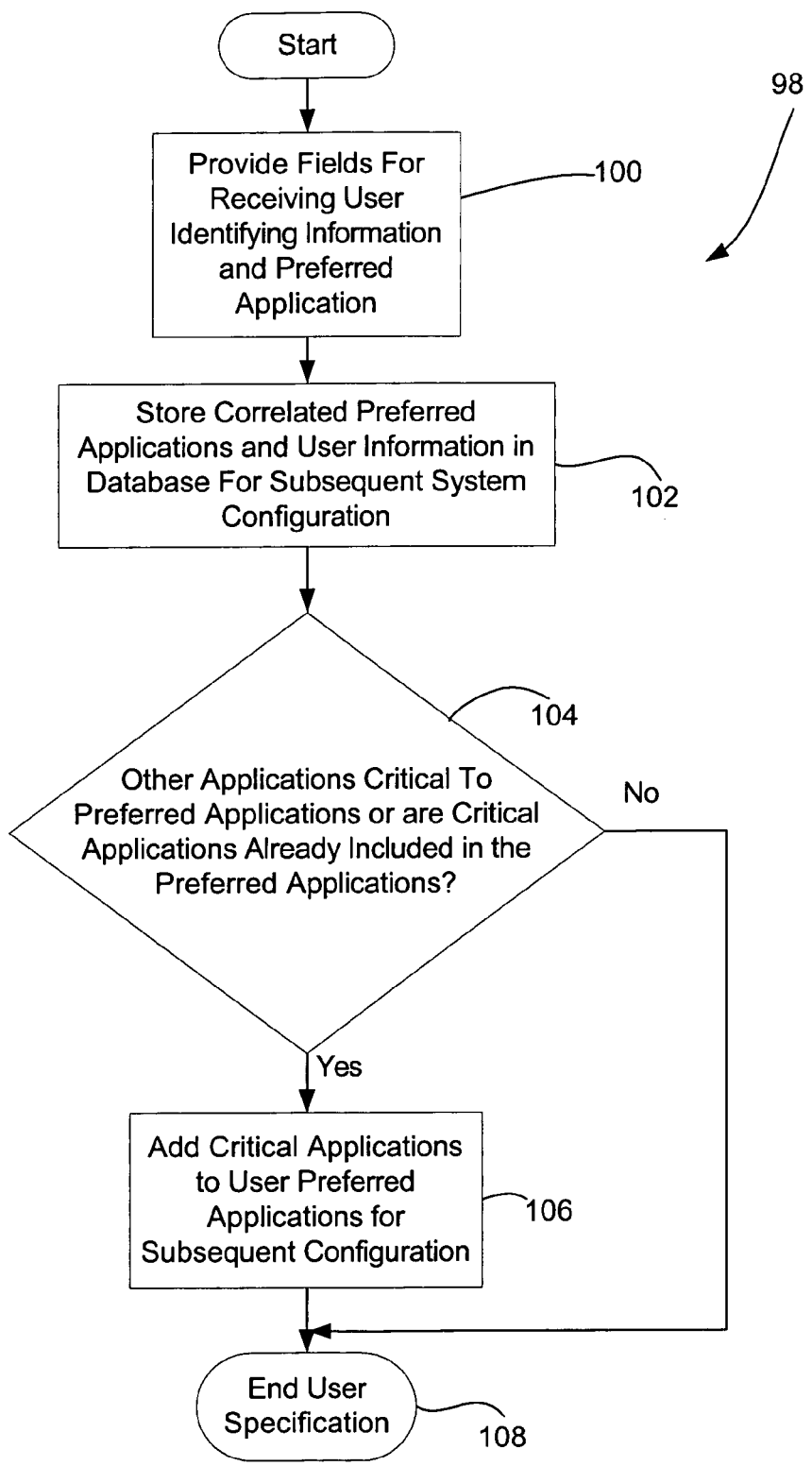
FIG. 2 is a flow chart illustrating one process performed using the system of FIG. 1.

Referring to FIG. 2 a process 98 for specifying specific user preferences is illustrated. To this end, referring also to FIG. 1, at the beginning of the specifying process 98 at block 100 server runs a data receiving application to provide fields for receiving user identifying information and preferred application information. Exemplary fields are illustrated in FIG. 1 as fields 30 and 32. The user identifying information may include the user's name, a physician ID number or some other uniquely identifying information. In the present example it is assumed that each physician will have a physician number (i.e., a number like the numbers in column 158 of database 156.

The preferred application information may include a simple list of numbers corresponding to preferred applications, each number separated from the following number by a comma (i.e., the information may resemble the list of applications I column 160 of database 156). In this case the user entering the preferred application list would have to have a separate key that could be used to correlate numbers with applications. Other more intuitive application specifying tools are contemplated including a tool whereby icons corresponding to each application are selected via clicking of a mouse button or some type of drag and drop sequence of icon selection.

Referring still to FIGS. 1 and 2 and also to FIG. 6, after a user has provided the required user identifying information and the preferred application information, the user submits the provided information to server 12. In the present example a "Submit" icon 34 is provided that, when selected, submits the information.

At block 102 server 12 correlates and stores the user identifying information with the preferred applications in database 156 for subsequent use in configuring system 10 whenever the specific user logs onto the system 10.

Next, at block 104 server 12 determines whether or not there are applications that are critical to operation of any of the user specified preferred applications. A critical application is an application that must be booted and capable of running for some other application to perform properly. For instance, one MRI application may be to excite system 18 coils with a specific pulse sequence to cause MRI signals to be generated. Another application may be an application for collecting the MRI data as the data is generated. Yet another application may be to compress the collected data in a specific manner so that all data collected during a single acquisition period is storable on local database 16 for subsequent manipulation. In this case the data collection application cannot function without the excitation application and the data will not be stored properly without the data compression application. Thus, where the collection application is selected, each of the excitation and compression applications is critical.

Where there are no applications that are critical to the user specified preferred applications or where the applications that are critical to user specified applications are included in the user specified applications, control passes to block 108 and the specifying process is complete.

However, where there are applications that are critical to user preferred applications that are not included in the preferred application list, control passes to block 106 and the critical applications are added to the user preferred application list for subsequent system 10 configuration. Thus, applications that ate critical to operation of user preferred applications are automatically included in the user preferred application list. Thus automated feature may be either transparent to the user during specification or the system may provide the user with an indication that additional critical applications have been added to the user's list of preferred applications.

Referring still to FIGS. 1 and 2 and also to FIGS. 5 and 6 an example of how process 98 works is helpful. To this end, assume that first user 00001 is using workstation 11 to specify preferred applications. Also assume that at block 100 user 00001 provides a list including applications 1, 2, 12, 17 and 20. Upon submitting the preferred applications list, at block 104 a processor inside server 12 accesses critical applications database 150 and determines whether or not, for each application in the user's preferred list, there are critical applications. In this example, referring to column 154, for application 1 there are two critical applications including applications 5 and 6. For this reason, at block 10-6 server 12 automatically adds critical applications 5 and 6 to the list of applications for the user. In FIG. 6 the resulting list of applications for user 00001 is illustrated with critical applications identified by italic and underlined numbers 5 and 6.

Referring still to FIG. 6, in a similar fashion user 00002 steps through the specifying process to provide the list of preferred applications in column 160. Note that in the case of user 00002, while applications 5 and 6 may be critical to application 1 (see also FIG. 5), applications 5 and 6 are not underlined and are not italicized thereby indicating that those applications where added to the preferred list by user selection and not due to criticality. With respect to user 00003 application 3 was selected by the user and therefore the configuration process automatically added critical applications 2 and 12 (see also FIG. 5 in this regard).

In addition to specifying user preferred applications it is contemplated that workstation 11 can also be used to set specific and preferred application parameters such as pulse sequences useable within an application, pulse strength, filtering parameters, image plane parameters, etc. While not illustrated this parameter setting capability is important for the same reasons that the application preference setting capability is important. Specifically, by recording preferred parameter settings for each system user the preferred setup configuration is achieved more quickly after user log on.

Moreover, other preferred system parameters can be set and recorded for subsequent expedited configuration. For example, in some cases it may be that certain applications must not be slowed or interrupted. For instance, a data acquisition application in an MRI system 10 cannot be hampered or slowed without losing valuable data required to generate images. In this case, assuming the acquisition application is one of several preferred applications, it may be that at some processor (i.e., server 12) load level less important applications should be disabled to ensure that the acquisition application is fully supported. Here, it is contemplated that workstation 11 could be used to set processor thresholds for less important applications at which the applications could be disabled to free up processor capacity and fully support the acquisition application. Thus, for instance, referring to user 00001 in FIG. 6 having preferred applications 1, 2, 5, 6, 12, 17 and 20, if application 17 is the least important and is not critical to other preferred applications, user 00001 may set the loading threshold at 70% so that server 12 would disable the application when the 70% threshold is met. Similarly, if application 12 is the second least important application a threshold for application 12 may be set to 75% and so on. The thresholding process is described in more detail below with respect to FIG. 7.

Figure 3:
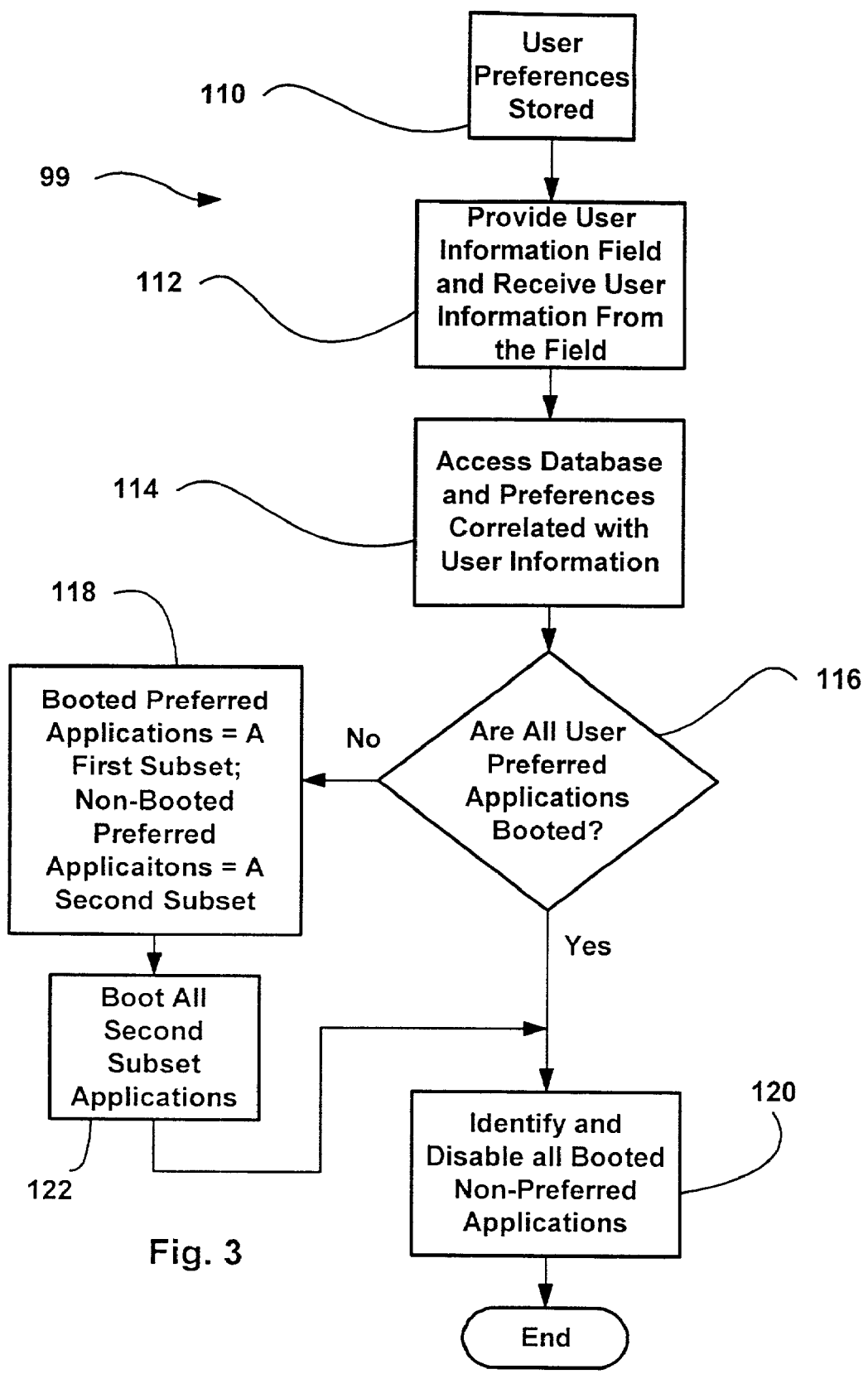
FIG. 3 is a flow chart illustrating another process performed using the system of FIG. 1.

Referring now to FIGS. 1 and 3, a process for automatically configuring system 10 upon a user logging onto system 10 is illustrated. In the case of medical imaging systems like system 10, these systems typically remain on all day, different physicians accessing the systems at different times to perform imaging processes. At the end of any imaging day it is assumed that system 10 is completely shut down.

Initially it is assumed that system user preferred application lists have been stored 110 for several system users (see, for example, FIG. 6). With system 10 shut down, when system 10 is first turned on, according to an exemplary embodiment of the invention, at block 112 server 12 provides a user information field (e.g., similar to filed 30 in FIG. 1) to the user for receiving user information (e.g., a user number).

Referring also to FIG. 6, after user information is received, at block 114 server 12 accesses database 156 and correlates the user information with a user preferred applications list in column 160. For the purposes of this explanation assume that user 00001 is the first user to start up system 10. Thus, the application list in this example includes applications 1, 2, 5, 6, 12, 17 and 20. Next, at block 116 server 12 determines whether or not all of the user preferred applications are booted. Where all applications are booted control passes to block 120.

In the present case, because system 10 was off prior to user 00001 starting up the system, control passes to block 118. At this point the user preferred applications are divided into first and second subsets including booted and non-booted preferred applications. Because all applications were off prior to user 00001 starting up the system, initially all preferred applications are included in the second subset.

At block 122 server 12 boots up all second subset applications. Booting an application includes causing the application to be opened and readied for use, typically by loading the application from database 42 onto database 16 for running by server 12.

In the present case each of applications 1, 2, 5, 6, 12, 17 and 20 are booted up and readied for use by user 00001. At block 120 server 120 identifies all booted applications that are non-preferred applications and disables the non-preferred booted applications. Disablement may take any of several different forms including simply minimizing the applications so that they do not run during subsequent imaging processes. In the alternative, removing the applications may include completely erasing the applications from the local database so as to free up storage space that, in some cases, can increase processing speed.

Next, assume that after the first imaging session performed by user 00001, user 00001 logs off system 10 prior to a second user 00002 logging onto system 10 to perform a second imaging process. In this case, when the first user logs off, while the imaging data and other data specific to the first imaging session may be erased from database 16, the preferred applications booted for the first user remain booted and ready for use if the second user's preferred applications list includes any of the already booted applications.

To this end, referring again to FIGS. 1, 3 and 6, when second user 00002 accesses workstation 11 and provides user identifying information to server 12, server 12 again accesses database 156 at block 114 and identifies second user 0002's preferred applications. In this case the user applications include applications 1, 2, 4, 5, 6, 7, 8, 9, 10 and 11. At block 116 server 12 compares the second user's applications to the booted applications and determines if any of the second user's preferred applications are not booted. In this case, because the first user used system 10 just prior to the second user 0002, comparing the preferred applications from the first and second users (see FIG. 6) indicates which of the second user's preferred applications are booted and which are not booted. Booted applications include applications 1, 2, 5 and 6 while non-booted applications include applications 4, 7, 8, 9, 10 and 11. Thus, consistent with block 118, the applications are divided into a first booted preferred subset and a second non-booted preferred subset. At block 122 all non-booted applications (i.e., applications in the second subset) are booted.

At block 120 server 12 identifies and disables all booted and non-preferred applications. In this case, again comparing the preferred applications for users 00001 and 00002, applications 12, 17 and 20 are booted but non-preferred. Therefore, at block 120 server 12 disables applications 12, 17 and 20.

It should be appreciated that the present system enables relatively fast system configuration by only booting up applications required by specific users as well as by maintaining booted applications in a ready state for subsequent users that may want to use the same applications. This fast booting feature has additional advantages during system maintenance. For example periodically field/service engineers have to run tests on imaging systems to determine if system operating parameters have to be adjusted or if hardware components have to be replaced. To perform these tests, as one would expect, certain applications and parameter settings are necessary. As in the case of different physicians using a system, when a service engineer uses a system the process is slowed if all applications are booted. The present invention, however, expedites the maintenance routine in a fashion similar to that described above. In addition, the system increases the speed of preferred applications by automatically disabling non-preferred applications. Moreover, the system facilitates relatively fast user specification of preferred applications by effectively causing critical applications to automatically enable to support other applications.

Figure 4:
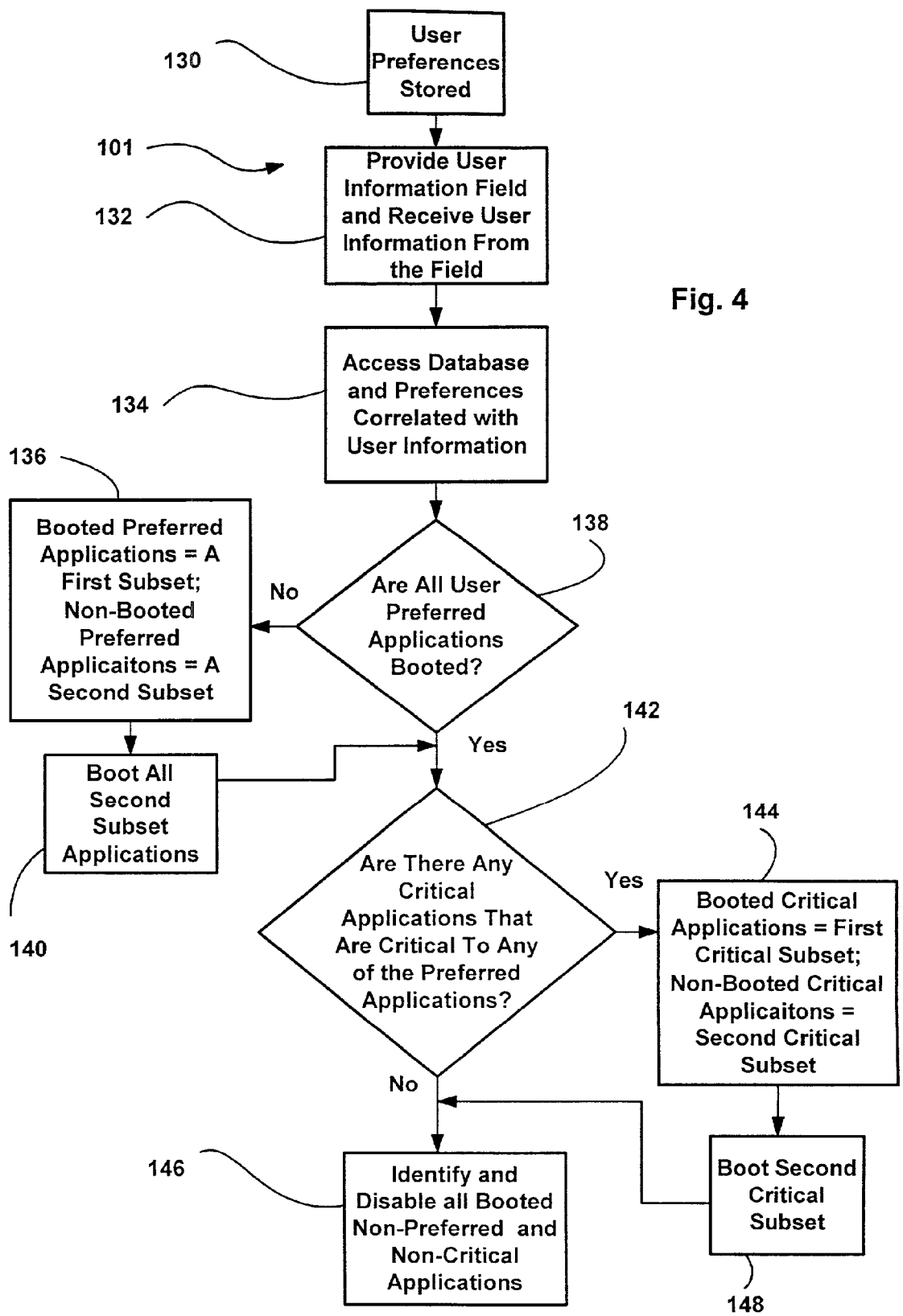
FIG. 4 is an alternative process similar to the process of FIG. 3.

While the exemplary embodiment of the invention described above includes the server adding critical applications to a user's preferred application list in database 156, other ways of accomplishing this same end result are also contemplated. For example, referring to FIG. 4 another way to ensure that critical applications are booted to support preferred applications is illustrated.

Referring also to FIGS. 1, 5 and 6, as in the method of FIG. 3, at block 130 it is assumed that user preferred applications have been specified. However, in this case, referring also to FIG. 2, instead of identifying critical applications and adding critical applications to the user preferred applications list at blocks 104 and 106, it is assumed that server 12 simply stored the user specified preferred applications for each user. Thus, in FIG. 6, only applications 1, 2, 12, 17 and 20 appear in column 160 corresponding to user 0001, all of applications 1, 2, 4, 5, 6, 7, 8, 9 ,10 and 11 appear correlated with user 00092 and only application 3 is correlated with user 00003. In other words, the critical applications 5 and 6 for user 00001 and 2 and 12 for user 00003 are not included in column 160.

For the purposes of this explanation assume that user 00002 just completed use of system 10 and has logged off so that applications 1, 2, 4, 5, 6, 7, 8, 9, 10 and 11 are all currently booted. Also assume that the next physician to use system 10 is user 00003. When user 0003 provides user information at block 132 to log onto system 10, server 12 uses the log on information to correlate user preferences with the user information at block 134. Thus, server 12 identifies preferred application 3 as the only preferred application for user 0003 (remember that applications 2 and 123 are critical to application 3—see also FIG. 5—but that they were not previously automatically added to the user preferred application list).

Next, at block 138 server 12 determines whether or not all of user 00003's preferred applications have been booted up. Comparing second user 00002's preferred applications to third user 00003's applications it can be seen that application 3 is not currently booted. Thus, control passes through block 136 to block 140 and application 3 is booted after which control passes to block 142.

At block 142 server 12 accesses database 150 to determine if there are any critical applications that must be booted to support preferred application 3. If there were no applications critical to application 3 control would pas to block 146. However, in the present case, in column 154 database 150 indicates that applications 2 and 12 are critical to operation of application 3 and therefore control passes to block 144.

At block 144 server 12 divides the critical applications into first and second critical application subsets including booted critical applications and non-booted critical applications, respectively. Continuing at block 148 server 12 boots all second critical subset applications. In the present case this means that server 12 boots each of applications 2 and 12 so that each of applications 2, 3 and 12 are booted and ready for use by user 00003. Control then passes to block 146.

At block 146 server 12 identifies and disables all booted non-preferred and non-critical applications. To this end, referring again to FIG. 6, because user 00002 used system 10 just prior to user 00003, in addition to applications 2 and 12, each of applications 1, 4, 5, 6, 7, 8, 9, 10 and 11 are booted despite being non-preferred. Thus, in this case server 12 disables each of applications 1, 4, 5, 6, 7, 8, 9,10 and 11 at block 146.

While the invention is described above in the context of server 12 performing a method, the invention also contemplates a processor within server 12 performing a pulse sequencing program that causes the processor to step through each the methods described above.

Figure 7:
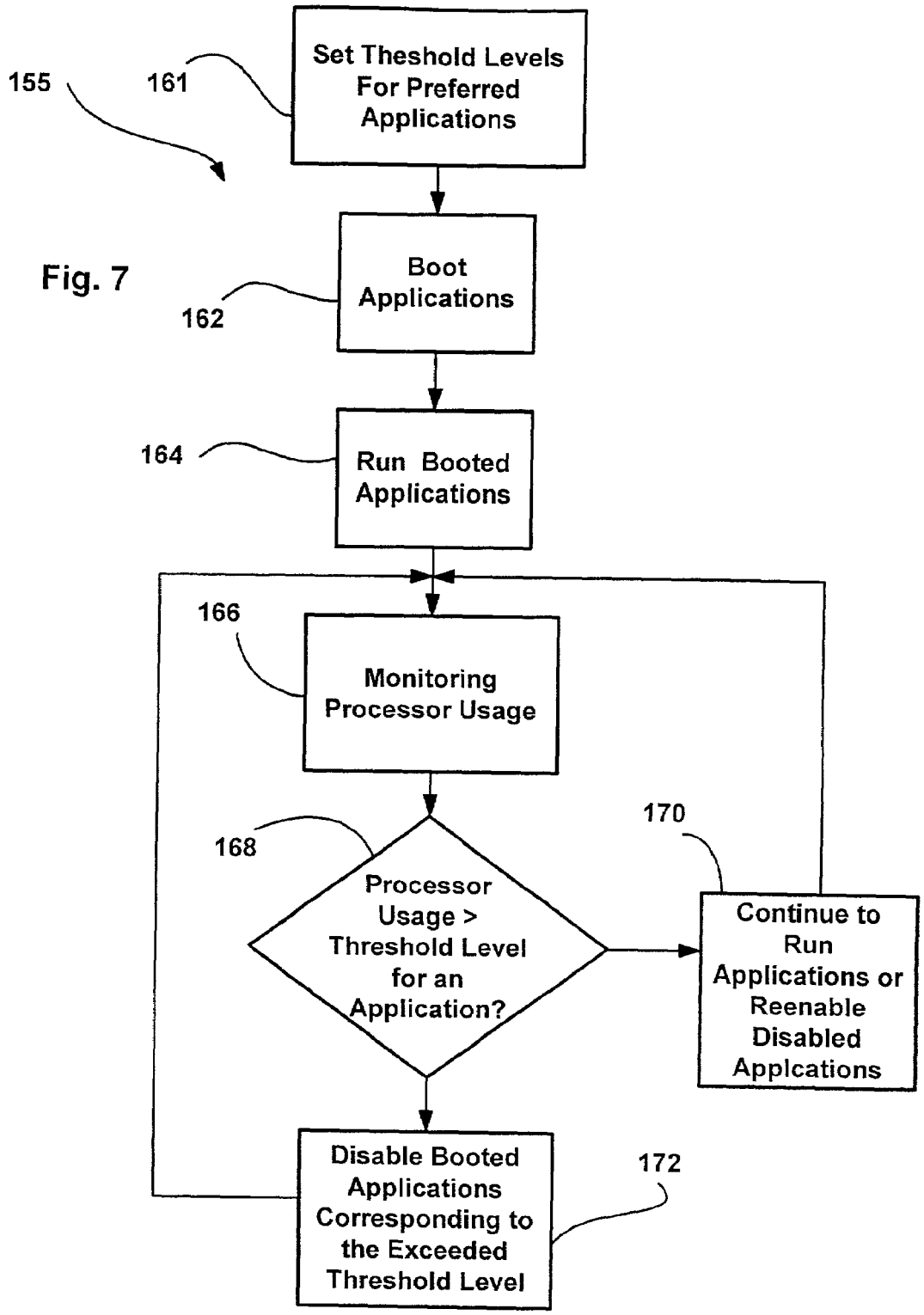
FIG. 7 is a flow chart illustrating yet another process performable by the system of FIG. 1.

Referring now to FIGS. 1 and 7, the process of modifying applications as a function of processor loading is described in the context of a method 155. At block 161 it is assumed that all threshold levels for a users preferred applications have been set during a previous specifying procedure similar to the procedure illustrated in FIG. 2. At block 162 server 12 boots all of a user's preferred applications in a manner similar to that described in FIG. 3. At block 164 the booted applications are performed while the system user interacts with the system to acquire data and/or manipulate data and observe resulting images. At block 166 processor usage is monitored.

At decision block 168 the processor usage is compared to each preferred application threshold level and, when a threshold level is exceeded, control passes to block 172. At block 172, for any application for which the threshold level has been exceeded, server 12 disables the application. Thus, for example, where threshold levels for applications 17 and 12 are 70% and 75%, respectively, when processor usage level exceeds 70%, server 12 disables application 17 and when processor usage level exceeds 75% server 12 disables application 12 and so on. After disabling control passes again back up to block 166 where processor usage is continually monitored.

Referring still to FIG. 7, assuming that each of applications 12 and 17 have already been disabled and that the next threshold (not illustrated) is not reached yet, control passes from block 166 to 168 and then to 170 where the applications that are still enabled continue to run with control cycling back to block 166. When processor usage again dips below the 75% threshold level, at block 170, server 12 re-enables application 12. Similarly, when processor usage again dips below the 70% threshold level, at block 170, server 12 re-enables application 17. If desired a difference between disabling and enabling thresholds may automatically be programmed into server 12 to facilitate hysteretic control and avoid hunting.

It should be appreciated that, while some time is required between imaging sessions to boot un-booted and preferred applications and to disable non-preferred and booted applications, the booting and disabling process can typically be performed simultaneously with patient positioning and other processes and therefore the duration of the booting and disabling process is essentially irrelevant.

It should be understood that the methods and apparatuses described above are only exemplary and do not limit the scope of the invention, and that various modifications could be made by those skilled in the art that would fall under the scope of the invention.

What is claimed is:

1. A method for configuring a set of applications in a medical imaging system, the method comprising the steps of:
  receiving system user identifying information;
  using the identifying information to determine the user's preferred applications;
  determining which of the preferred applications are already booted up, the already booted up preferred applications being a first subset and the other preferred applications being a second subset;
  booting up the second subset of preferred applications;
  identifying non-preferred applications that are booted; and
  disabling the non-preferred applications.

2. The method of claim 1 wherein the step of disabling includes turning off the non-preferred applications.

3. The method of claim 1 also for use with a database including user-identifying information correlated with preferred applications and wherein the step of using includes correlating the identifying information with the preferred applications.

4. The method of claim 1 wherein the step of receiving includes providing at least one field for entering user identifying information on a display and, when information is provided via the field, retrieving the information therefrom.

5. The method of claim 1 wherein at least one critical application is critical to operation of at least one of the preferred applications and wherein the method further includes the steps of, for each preferred application, determining if there are any critical applications and for critical applications determining which of the critical applications is booted up, the booted up critical applications being a first subset of critical applications and all other critical applications being a second subset of critical applications, the method further including booting up all second subset critical applications.

6. The method of claim 1 also for configuring the user preferred applications, the method further including the steps of, providing an interface for receiving user information and preferences, receiving user preferences and related user information via the interface and storing the user preferred applications correlated with the user information for subsequent use.

7. The method of claim 6 wherein there is at least one critical application that is critical to operation of at least one user specified preferred application and wherein the method further includes the steps of, for each specified preferred application, determining if there are any critical applications and, where there is at least one critical application, adding the critical application to the preferred applications for the user.

8. The method of claim 1 wherein the system includes a processor for running the applications and where the method is also for modifying the booted applications as a function of processor usage and, wherein, the method further includes the steps of, after the applications are booted and during system use, monitoring processor usage and, when processor usage exceeds a threshold level, disabling at least one of the booted applications.

9. A processor for use in configuring a set of applications in a medical imaging system, the processor running a pulse sequencing program to perform steps comprising:
  receiving system user identifying information;
  using the identifying information to determine the user's preferred applications;
  determining which of the preferred applications are already booted up, the already booted up preferred applications being a first subset and the other preferred applications being a second subset;
  booting up the second subset of preferred preferences;
  identifying non-preferred applications that are booted; and
  disabling the non-preferred applications.

10. The processor of claim 9 wherein the step of disabling includes turning off the non-preferred applications.

11. The processor of claim 9 also for use with a database including user-identifying information correlated with preferred applications and wherein the step of using includes correlating the identifying information with the preferred applications.

12. The processor of claim 9 wherein at least one critical application is critical to operation of at least one of the preferred applications and wherein the program further causes the processor to perform the steps of, for each preferred application, determining if there are any critical applications and for critical applications determining which of the critical applications is booted up, the booted up critical applications being a first subset of critical applications and all other critical applications being a second subset of critical applications, the processor further including booting up all second subset critical applications.

13. The processor of claim 9 also for specifying the user preferred applications, the program further causing the processor to perform the steps of, providing an interface for receiving user information and preferences, receiving user preferences and related user information via the interface and storing the user preferred applications correlated with the user information for subsequent use.

14. The processor of claim 13 wherein there is at least one critical application that is critical to operation of at least one user specified preferred application and wherein the processor further includes the steps of, for each specified preferred application, determining if there are any critical applications and, where there is at least one critical application, adding the critical application to the preferred applications for the user.

15. The processor of claim 9 wherein the system includes a processor for running the applications and where the processor is also for modifying the booted applications as a function of processor usage and, wherein, the processor further includes the steps of, after the applications are booted and during system use, monitoring processor usage and, when processor usage exceeds a threshold level, disabling at least one of the booted applications.

16. A method for configuring a set of applications in a medical imaging system, the method comprising the steps of:
receiving system user identifying information;
using the identifying information to determine the user's preferred applications;
determining which of the preferred applications are already booted up, the already booted up preferred applications being a first subset and the other preferred applications being a second subset;
booting up the second subset of preferred preferences;
identifying non-preferred applications that are booted; and
disabling the non-preferred applications.

17. A method for specifying a set of user preferred applications in a medical imaging system wherein at least one critical application is critical to operation of at least one other application, the method comprising the steps of:
receiving system user identifying information;
receiving user preference information indicating at least one user preferred application;
storing the user identifying information correlated with the user preferred applications for subsequent system configuration upon booting;
determining if there are any applications that are critical to the user preferred applications; and
where an application is critical to a user-preferred application, adding the critical application to the user stored preferred applications correlated with the user.

18. An apparatus for configuring a set of applications in a medical imaging system, the apparatus comprising:
means for receiving system user identifying information;
means for using the identifying information to determine the user's preferred applications;
means for determining which of the preferred applications are already booted up, the already booted up preferred applications being a first subset and the other preferred applications being a second subset;
means for booting up the second subset of preferred applications;
means for identifying non-preferred applications that are booted; and
means for disabling the non-preferred applications.

* * * * *